(12) United States Patent
Sweeney

(10) Patent No.: US 8,527,047 B2
(45) Date of Patent: Sep. 3, 2013

(54) ARTIFICIAL CONDUCTION PATHWAYS IN TACHYARRHYTHMIA

(75) Inventor: Robert J. Sweeney, Woodbury, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 525 days.

(21) Appl. No.: 12/751,972

(22) Filed: Mar. 31, 2010

(65) Prior Publication Data

US 2010/0286737 A1 Nov. 11, 2010

Related U.S. Application Data

(60) Provisional application No. 61/177,112, filed on May 11, 2009.

(51) Int. Cl.
*A61N 1/365* (2006.01)

(52) U.S. Cl.
USPC .................................. 607/14; 607/9

(58) Field of Classification Search
USPC ....................................... 607/2–17
See application file for complete search history.

(56) References Cited

U.S. PATENT DOCUMENTS

| | | | |
|---|---|---|---|
| 6,081,746 A | 6/2000 | Pendekanti et al. | |
| 6,085,116 A | 7/2000 | Pendekanti et al. | |
| 6,292,691 B1 | 9/2001 | Pendekanti et al. | |
| 6,400,986 B1 | 6/2002 | Sun et al. | |
| 6,473,645 B1 | 10/2002 | Levine | |
| 6,484,057 B2 | 11/2002 | Ideker et al. | |
| 6,654,639 B1 | 11/2003 | Lu | |
| 6,704,598 B2 * | 3/2004 | Ding et al. | 607/9 |
| 6,731,982 B1 | 5/2004 | Kroll et al. | |
| 6,754,531 B1 | 6/2004 | Kroll et al. | |
| 6,766,196 B1 | 7/2004 | Kroll et al. | |
| 6,801,806 B2 | 10/2004 | Sun et al. | |
| 6,907,286 B1 | 6/2005 | Kroll et al. | |
| 7,050,852 B2 | 5/2006 | Zhu et al. | |
| 7,295,873 B1 | 11/2007 | Min et al. | |
| 7,353,060 B2 | 4/2008 | Sun et al. | |
| 7,376,464 B2 | 5/2008 | Quigsheng et al. | |
| 7,392,082 B2 | 6/2008 | Sharma | |
| 7,457,664 B2 | 11/2008 | Zhang et al. | |
| 2002/0058968 A1 * | 5/2002 | Sun et al. | 607/14 |
| 2004/0127946 A1 * | 7/2004 | Wagner et al. | 607/5 |
| 2004/0172065 A1 | 9/2004 | Sih et al. | |
| 2004/0210257 A1 | 10/2004 | Havel et al. | |

* cited by examiner

*Primary Examiner* — Allen Porter, Jr.
(74) *Attorney, Agent, or Firm* — Schwegman Lundberg & Woessner, P.A.

(57) ABSTRACT

An implantable medical device can establish one or more artificial conduction pathways during tachyarrhythmia. Withdrawal of the artificial conduction pathway may help self-terminate the tachyarrhythmia, or may pre-condition the tachyarrhythmia to be more favorable for receiving an anti-tachyarrhythmia therapy, such as anti-tachyarrhythmia pacing, defibrillation shock therapy, or cardioversion. This can help provide enhanced anti-tachyarrhythmia therapy.

19 Claims, 4 Drawing Sheets

ARTIFICIAL CONDUCTION PATHWAYS IN TACHYARRHYTHMIA

CROSS-REFERENCE TO RELATED APPLICATION

This application claims the benefit of U.S. Provisional Application No. 61/177,112, filed on May 11, 2009, under 35 U.S.C. §119(e), which is hereby incorporated by reference in its entirety.

BACKGROUND

Implantable medical devices (IMDs) are devices designed to be implanted into a patient. Some examples of these devices include implantable cardiac rhythm management (CRM) devices such as implantable pacemakers, implantable cardioverter defibrillators (ICDs), implantable cardiac resynchronization devices, or devices that include a combination of such capabilities. The devices can be used to treat patients using electrical or other therapy or to aid a physician or caregiver in patient diagnosis such as through internal monitoring of a patient's condition. The devices can include one or more electrodes in communication with one or more sense amplifiers to monitor electrical heart activity within a patient, and often include one or more sensors to monitor one or more other physiological patient parameters. Other examples of implantable medical devices include implantable diagnostic devices, implantable drug delivery systems, or implantable devices with neural stimulation capability, some of which can also be CRM devices.

Additionally, some CRM devices detect events by monitoring electrical heart activity signals, such as heart chamber expansions or contractions. By monitoring cardiac signals indicative of expansions or contractions, IMDs can detect tachyarrhythmia. Tachyarrhythmia includes abnormally rapid heart rate, such as ventricular tachyarrhythmia (VT), supraventricular tachyarrhythmia (SVT), and sinus tachyarrhythmia (ST). Tachyarrhythmia also includes rapid and irregular heart rate, or fibrillation, such as ventricular fibrillation (VF).

Some CRM devices are able to provide therapy for tachyarrhythmia, such as anti-tachyarrhythmia pacing (ATP) or high energy shock therapy. A therapy approach for a VT can include providing ATP to attempt to terminate the tachyarrhythmia. If ATP fails to terminate the tachyarrhythmia after an appropriate amount of time, then shock therapy (e.g., cardioversion or defibrillation) can be introduced, such as via a CRM device.

OVERVIEW

This document describes, among other things, an implantable medical device capable of establishing one or more artificial conduction pathways during tachyarrhythmia. Withdrawal of the artificial conduction pathway may help self-terminate the tachyarrhythmia, or may pre-condition the tachyarrhythmia to be more favorable for receiving an anti-tachyarrhythmia therapy, such as anti-tachyarrhythmia pacing, defibrillation shock therapy, or cardioversion. This can help provide enhanced anti-tachyarrhythmia therapy.

Example 1 describes an implantable medical device. In this example, the device comprises a tachyarrhythmia detection circuit configured to detect a presence of a tachyarrhythmia in a subject; a sensing circuit, coupled to the tachyarrhythmia detection circuit, configured to be coupled to a first electrode and a second electrode, wherein the first electrode is configured to be located at a first location in association with a heart of the subject and the second electrode is configured to be located at a second location in association with the heart, and wherein the sensing circuit is configured to sense, in response to and during the tachyarrhythmia, an intrinsic electrical heart depolarization at the first electrode and an intrinsic electrical heart depolarization at the second electrode; a processor circuit, coupled to the sensing circuit and the tachyarrhythmia detection circuit, configured to determine an intrinsic first time delay between the sensing of the intrinsic electrical heart depolarization at the first electrode and the sensing of the intrinsic electrical heart depolarization at the second electrode; an electrostimulation generator circuit, coupled to the processor circuit, configured to: deliver a plurality of electrostimulations using the first electrode; and trigger timing of the delivery of an individual electrostimulation in the plurality of electrostimulations, on a beat-by-beat basis, from a respective sensed intrinsic electrical heart depolarization at the second electrode, the timing including a specified second timing delay, from the respective sensed intrinsic electrical heart depolarization at the second electrode, that is specified to be approximately equal to the determined intrinsic first time delay between the sensing of the intrinsic electrical heart depolarization at the first electrode and the sensing of the intrinsic electrical second time delay at the second electrode; and an anti-tachyarrhythmia therapy circuit, coupled to the processor circuit, configured to provide anti-tachyarrhythmia therapy within a specified time in response to and after termination of the delivery of the plurality of electrostimulations.

In Example 2, the device of Example 1 optionally comprises the intrinsic electrical heart depolarization sensed at the first electrode being the same intrinsic electrical heart depolarization sensed at the second electrode.

In Example 3, the device of one or more of Examples 1-2 optionally comprises the processor circuit configured to determine the specified second timing delay, the specified second timing delay being specified to be within fifty percent of the determined intrinsic first time delay between the sensing of the intrinsic electrical heart depolarization at the first electrode and the intrinsic electrical heart depolarization at the second electrode.

In Example 4, the device of one or more of Examples 1-3 optionally comprises the processor circuit configured to determine the specified second timing delay, the specified second timing delay being a fixed and determined value.

In Example 5, the device of one or more of Examples 1-4 optionally comprises the processor circuit configured to determine the specified second timing delay, the specified second timing delay being adjustable over time.

In Example 6, the device of one or more of Examples 1-5 optionally comprises the processor circuit configured to decrease the timing delay in response to a sensed intrinsic heart depolarization at the first electrode during the delivery of the plurality of electrostimulations, wherein the processor circuit is configured to increase the timing delay in response to an absence of a sensed intrinsic heart depolarization at the first electrode during the delivery of the plurality of electro stimulations.

In Example 7, the device of one or more of Examples 1-6 optionally comprises the processor circuit configured to determine a central tendency of a plurality of measurements of the determined intrinsic first time delay between the sensing of the intrinsic electrical heart depolarization at the first electrode and the sensing of the intrinsic electrical heart depolarization at the second electrode, wherein the processor circuit is configured to determine the specified second timing delay, the specified second timing delay being shorter than a central tendency of the determined intrinsic first time delay between the sensing of the intrinsic electrical heart depolarization at the first electrode and the sensing of the intrinsic electrical heart depolarization at the second electrode.

In Example 8, the device of one or more of Examples 1-7 optionally comprises the anti-tachyarrhythmia therapy circuit configured to provide anti-tachyarrhythmia therapy within one cardiac cycle after and in response to the termination of the delivery of the plurality of electrostimulations.

In Example 9, the device of one or more of Examples 1-8 optionally comprises the anti-tachyarrhythmia therapy circuit configured to provide at least one of anti-tachyarrhythmia pacing, defibrillation shock therapy, or cardioversion within two cardiac cycles after and in response to the termination of the delivery of the plurality of the electrostimulations.

In Example 10, the device of one or more of Examples 1-9 optionally comprises the first electrode and the second electrode.

In Example 11, the device of one or more of Examples 1-10 optionally comprises the processor circuit configured to determine the specified second timing delay, the specified second timing delay being at least one of fixed and determined, adjustable over time, within fifty percent of the determined intrinsic first time delay, or shorter than a central tendency of a plurality of measurements of the determined intrinsic first time delay; wherein the anti-tachyarrhythmia therapy circuit is configured to provide anti-tachyarrhythmia therapy within a specified number of cardiac cycles after and in response to the termination of the delivery of the plurality of electrostimulations.

Example 12 describes an apparatus. In this example, the apparatus comprises means for determining that a tachyarrhythmia is present in a subject; means for sensing, in response to and during the tachyarrhythmia, an intrinsic electrical heart depolarization at a first electrode that is located at a first location in association with a heart of the subject; means for sensing, in response to and during the tachyarrhythmia, an intrinsic electrical heart depolarization at a second electrode that is located at a different second location in association with the heart; means for determining an intrinsic first time delay between the sensing of the intrinsic electrical heart depolarization at the first electrode and the sensing of the intrinsic electrical heart depolarization at the second electrode; means for delivering a plurality of electrostimulations using the first electrode, including triggering timing of the delivery of an individual electrostimulation in the plurality of electrostimulations, on a beat-by-beat basis, from a respective sensed intrinsic electrical depolarization at the second electrode, the timing including a specified second timing delay, from the respective sensed intrinsic electrical depolarization at the second electrode, that is specified to be approximately equal to the determined intrinsic first time delay between the sensing of the intrinsic electrical heart depolarization at the first electrode and the sensing of the intrinsic electrical heart depolarization at the second electrode; and means for providing anti-tachyarrhythmia therapy within a specified time after and in response to terminating the delivery of the plurality of electrostimulations.

In Example 13, the apparatus of Example 12 optionally comprises the means for delivering a plurality of electrostimulations using the second electrode including the specified second timing delay being at least one of fixed and determined, adjustable over time, within fifty percent of the determined intrinsic first time delay, or shorter than a central tendency of a plurality of measurements of the determined intrinsic first time delay; wherein the means for providing anti-tachyarrhythmia therapy includes means for providing anti-tachyarrhythmia therapy within a specified number of cardiac cycles after and in response to the termination of the delivery of the plurality of electrostimulations.

Example 14 describes a method. In this example, the method comprises determining that a tachyarrhythmia is present in a subject; and in response to and during the tachyarrhythmia: sensing an intrinsic electrical heart depolarization at a first electrode that is located at a first location in association with a heart of the subject; sensing an intrinsic electrical heart depolarization at a second electrode that is located at a different second location in association with the heart; determining an intrinsic first time delay between the sensing of the intrinsic electrical heart depolarization at the first electrode and the sensing of the intrinsic electrical heart depolarization at the second electrode; delivering a plurality of electrostimulations using the first electrode, including triggering timing of the delivery of an individual electrostimulation in the plurality of electrostimulations, on a beat-by-beat basis, from a respective sensed intrinsic electrical depolarization at the second electrode, the timing including a specified second timing delay, from the respective sensed intrinsic electrical depolarization at the second electrode, that is specified to be approximately equal to the determined intrinsic first time delay between the sensing of the intrinsic electrical heart depolarization at the first electrode and the sensing of the intrinsic electrical heart depolarization at the second electrode; and within a specified time after and in response to terminating the delivery of the plurality of electrostimulations, providing anti-tachyarrhythmia therapy.

In Example 15, the method of Example 14 optionally comprises sensing the same intrinsic electrical heart depolarization at the first and second electrodes.

In Example 16, the method of one or more of Examples 14-15 optionally comprises the specified second timing delay being specified to be within fifty percent of the determined intrinsic first time delay between the sensing of the intrinsic electrical heart depolarization at the first electrode and the sensing of the intrinsic electrical heart depolarization at the second electrode.

In Example 17, the method of one or more of Examples 14-16 optionally comprises the specified second timing delay being a fixed and determined value.

In Example 18, the method of one or more of Examples 14-17 optionally comprises the specified second timing delay being adjustable over time.

In Example 19, the method of one or more of Examples 14-18 optionally comprises decreasing the specified second timing delay in response to a sensed intrinsic heart depolarization at the first electrode during the delivery of the plurality of electrostimulations; and increasing the specified second timing delay in response to an absence of a sensed intrinsic heart depolarization at the first electrode during the delivery of the plurality of electrostimulations.

In Example 20, the method of one or more of Examples 14-19 optionally comprises determining a central tendency of a plurality of measurements of the determined intrinsic first time delay between the sensing of the intrinsic electrical heart depolarization at the first electrode and the sensing of the intrinsic electrical heart depolarization at the second electrode, and wherein triggering timing of the delivery of an individual electrostimulation in the plurality of electrostimulations includes the specified second timing delay being shorter than a central tendency of the determined intrinsic first time delay between the sensing of the intrinsic electrical heart depolarization at the first electrode and the sensing of the intrinsic electrical heart depolarization at the second electrode.

In Example 21, the method of one or more of Examples 14-20 optionally comprises providing anti-tachyarrhythmia therapy within one cardiac cycle after the termination of the delivery of the plurality of electrostimulations.

In Example 22, the method of one or more of Examples 14-21 optionally comprises providing at least one of anti-tachyarrhythmia pacing, defibrillation shock therapy, or cardioversion within two cardiac cycles after the termination of the delivery of the plurality of the electrostimulations.

This overview is intended to provide an overview of subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

The present inventor has recognized, among other things, that using an "artificial conduction pathway," such as described below, can be used to enhance anti-tachyarrhythmia therapy or to help reduce cardioversion or defibrillation energy used to effectively terminate a tachyarrhythmia, which, in turn, can increase the useful life of an implantable CRM device.

This document describes, among other things, using an artificial conduction pathway (ACP) in anti-tachyarrhythmia therapy. By providing, then discontinuing, an ACP, a post-ACP time interval can be established, during which time it is believed that anti-tachyarrhythmia pacing, defibrillation, or cardioversion can be more effective.

During tachyarrhythmia, the spatiotemporal propagation of cardiac tissue depolarizations generally continuously changes or varies. Depolarization in one area of the heart can influence depolarization in one or more other areas of the heart. Thus, the time between depolarization at one location in the heart, e.g., location A, and depolarization at another location in the heart, e.g., location B, can vary from one cardiac cycle to the next. This variability can be due to how local tissue properties along the conduction path can affect the spatiotemporal nature of the depolarization.

An ACP can be established during a tachyarrhythmia, such as by providing an electrostimulation to location B that is triggered and timed from a sensed depolarization at location A. It is believed that this can cause the time between the depolarization at location A and the electrostimulation-evoked depolarization at location B to become fixed and controllable. It is believed that providing one or more ACPs during a tachyarrhythmia can result in the tachyarrhythmia depolarization propagation pathways incorporating or "becoming dependent" on the ACP. Without being bound by theory, this can be conceptualized as an ACP representing a more reliable pathway for the arrhythmia, due to the ACP's fixed and predictable timing. It is believed that, when one or more ACPs is provided, and then suddenly discontinued, the cardiac tissue that was dependent on the ACP can become more susceptible to anti-tachyarrhythmia therapy, such as ATP, cardioversion, or defibrillation, because of a transient increase in the amount of excitable tissue that would otherwise have been depolarized by the ACP. In this way, an ACP can be used to pre-condition the tachyarrhythmia for delivering the anti-tachyarrhythmia therapy.

Figure 1:
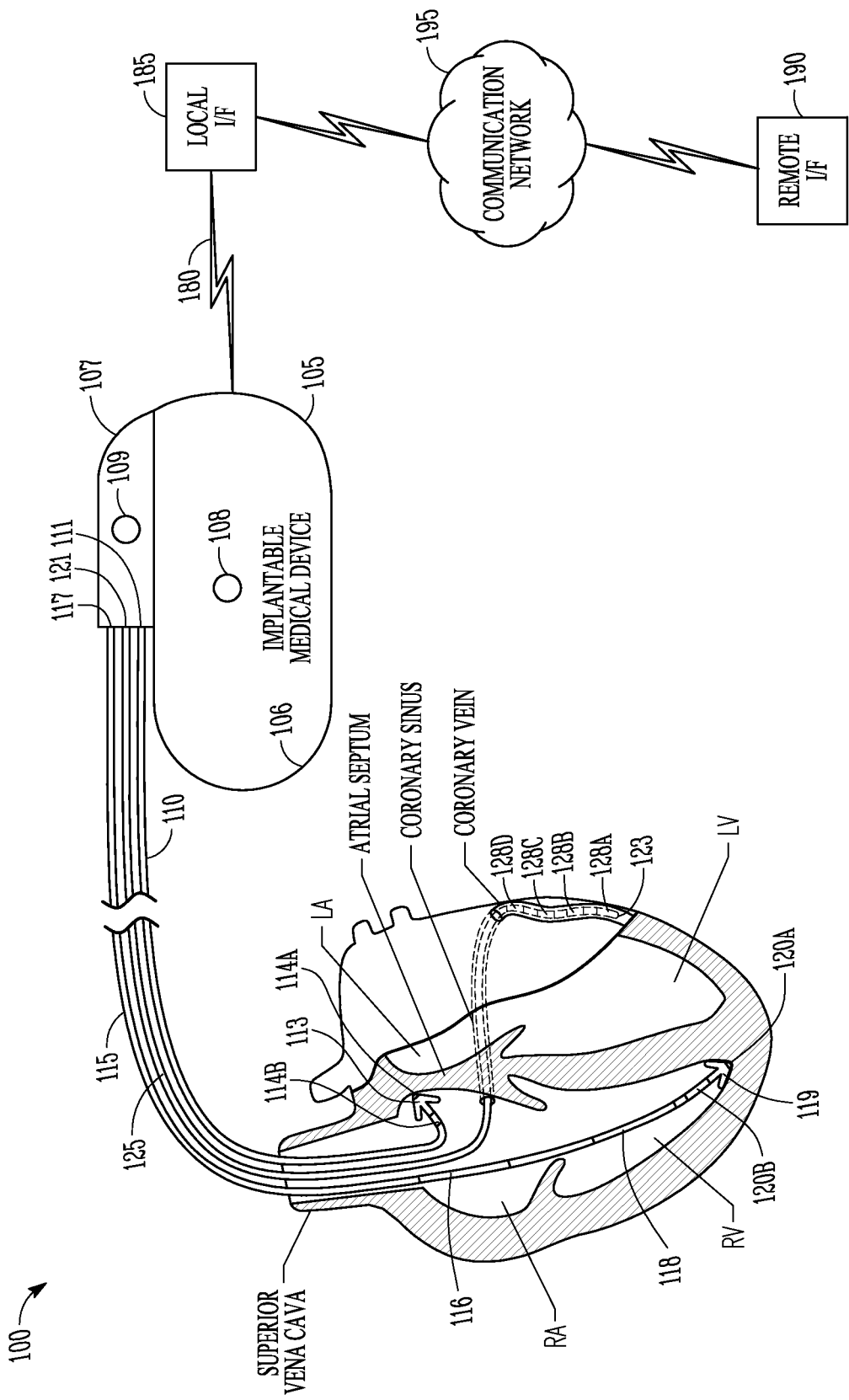
FIG. 1 is a schematic diagram illustrating generally an example of portions of a system that uses an implantable medical device (IMD).

FIG. 1 illustrates portions of a system 100 that can use an implantable medical device (IMD) 105. Examples of IMD 105 can include, without limitation, a pacemaker, a cardioverter, a defibrillator, a cardiac resynchronization therapy (CRT) device, or other cardiac monitoring and therapy delivery devices, including cardiac devices that include or work in coordination with one or more neuro-stimulating devices, drugs, drug delivery systems, or other therapies. In an example, the system 100 shown can be used to treat a cardiac tachyarrhythmia. The IMD 105 can include an electronics unit that can be coupled by one or more cardiac leads 110, 115, 125, to a heart of a patient or subject. The electronics unit of the IMD 105 can include components enclosed in an enclosure such as a hermetically-sealed canister or "can" 106. The can 106 can include one or more feedthroughs to a header 107. The header 107 can include one or more receptacles such as for receiving a proximal portion of one or more of the leads 110, 115, 125. One or both of the can 106 or header 107 can also include one or more additional electrodes, 108 or 109, respectively, such as for sensing intrinsic heart or other signals or for delivering stimulation or other energy to the patient. In addition or as an alternative, the can 106 itself can serve as an electrode.

The system 100 can also include a communication circuit, such as for establishing a unidirectional or bidirectional wireless communication link 180 with an external local interface 185. In an example, the external local interface can unidirectionally or bidirectionally communicate with an external remote interface 190, wirelessly or otherwise, such as via a shared communication or computer network 195. An example of using such a communication network 195 can include using the Boston Scientific Corp. (Cardiac Pacemakers, Inc.) LATITUDE® Patient Monitoring System. This can provide remote patient monitoring, such as by automatically collecting information from a patient's IMD 105 and communicating the information to a secure website accessible by the patient's healthcare providers. The external local interface 185, communication network 195, and remote interface 190 can also be used to communicate diagnostic information obtained from the patient's IMD 105, such as the presence or absence of a tachyarrhythmia.

The example shown includes right atrial (RA) lead 110 having a proximal end 111 and a distal end 113. The proximal end 111 can be coupled to a header connector 107 of the IMD 105. The distal end 113 can be configured for placement in the RA in or near the atrial septum. The RA lead 110 can include a pair of bipolar electrodes, such as an RA tip electrode 114A and an RA ring electrode 114B. The RA electrodes 114A and 114B can be incorporated into the lead body at the distal end 113 such as for placement at or near the atrial septum, and can each be electrically coupled to IMD 105 through a conductor extending within the lead body. The RA lead is shown placed at or near the atrial septum, but the RA lead can be placed at or near the atrial appendage.

The example shown can also include a right ventricular (RV) lead 115 having a proximal end 117 and a distal end 119. The proximal end 117 can be coupled to the header 107. The distal end 119 can be configured for placement in the RV. The RV lead 115 can include one or more of a proximal defibrillation electrode 116, a distal defibrillation electrode 118, an RV tip electrode 120A, or an RV ring electrode 120B. The defibrillation electrode 116 can be incorporated into the lead body such as at a location suitable for supraventricular placement in the RA or the superior vena cava. The defibrillation electrode 118 can be incorporated into the lead body near the distal end 119 such as for placement in or near the RV. The RV electrodes 120A and 120B can form a bipolar electrode pair and can be incorporated into the lead body at the distal end 119. The electrodes 116, 118, 120A, and 120B can each be electrically coupled to the IMD 105 such as through a respective conductor extending within the lead body. The proximal defibrillation electrode 116, distal defibrillation electrode 118, or an electrode 108 formed on the can 106 of the IMD 105 or an electrode 109 formed on the header 107 of the IMD 105 can be provided such as to allow for delivery of cardioversion/defibrillation pulses to the heart.

The RV tip electrode 120A, RV ring electrode 120B, or an electrode formed on the can of IMD 105 can allow for sensing an RV electrogram indicative of RV depolarizations or for delivering RV pacing or other pulses. The RA tip electrode 114A, the RA ring electrode 114B, or an electrode 108 formed on the can 106 of IMD 105 or an electrode 109 formed on the header 107 of IMD 105 can allow for sensing an RA electrogram indicative of RA depolarizations or delivering RA pacing or other pulses. Sensing and pacing can allow the IMD 105 to adjust timing or the spatial nature of the heart chamber contractions. In an example, the IMD 105 can adjust the timing delay of a ventricular contraction with respect to the timing of a preceding atrial contraction such as by sensing a contraction in the RA and pacing the RV at the desired atrial-ventricular (AV) delay time.

Also shown is a left ventricular (LV) lead 125. The LV lead 125 can include a coronary pacing or sensing lead that can include an elongate lead body having a proximal end 121 and a distal end 123. The proximal end 121 can be coupled to the header 107. The distal end 123 can be configured for placement or insertion in a coronary vessel, such as the into the great cardiac vein via the coronary sinus. The LV lead 125 can include an LV ring or tip electrode 128A or LV ring electrodes 128B, 128C, or 128D. The distal portion of LV lead 125 can be configured for placement in the coronary sinus and coronary vein such that the LV electrodes 128A, 128B, 128C, or 128D can be placed in the coronary vein. The LV electrodes 128A, 128B, 128C, or 128D can form a quadripolar electrode formation and can be incorporated into the lead body at the distal end 123 and each electrically coupled to the IMD 105 through a conductor extending within the lead body. The LV tip electrode 128A, the LV ring electrodes 128B, 128C, or 128D, or an electrode 108 formed on the can 106 of IMD 105 or an electrode 109 formed on the header 107 of IMD 105 can allow for sensing an LV electrogram indicative of LV depolarizations or delivering LV pacing pulses.

Other forms of electrodes can include meshes or patches, which can be applied to one or more portions of the heart, or electrodes that can be implanted in one or more other areas of the body such as for sensing or to help "steer" electrical current produced by the IMD 105 in FIG. 1. The IMDs can be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes).

Figure 2:
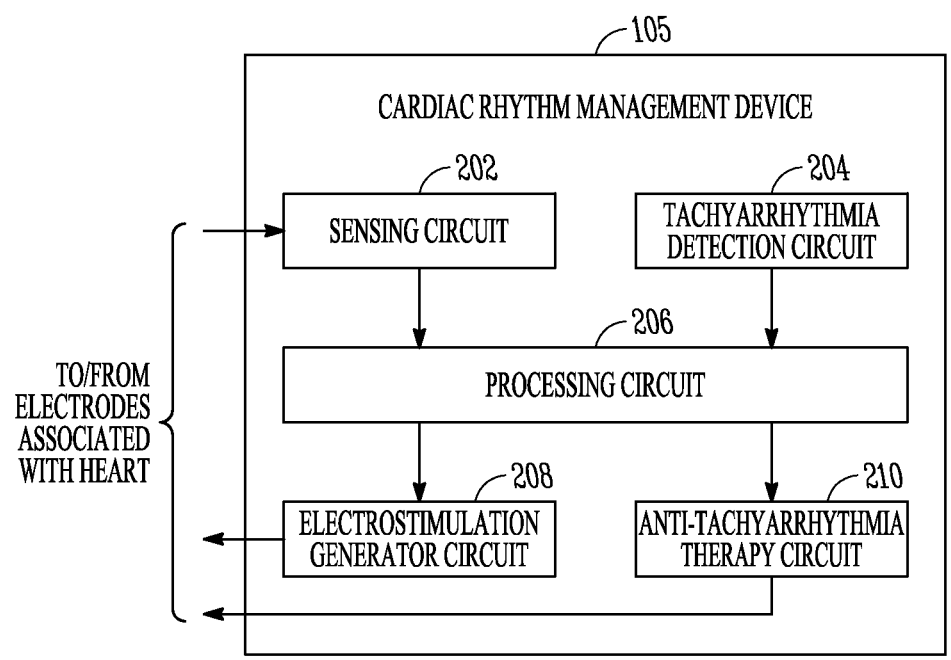
FIG. 2 is a schematic diagram illustrating further details of an example of portions of the system.

FIG. 2 is a schematic diagram of the IMD 105, which, in this example, is a CRM device. A sensing circuit 202 can be configured to be coupled to a first electrode and a second electrode, each of which is located at a separate and distinct location from each other at or in a patient's heart. For example, the first electrode can be any one of electrodes 114A, 114B, 116, 118, 120A, 120B, 128A, 128B, 128C, 128D, or the can 106 itself, and the second electrode can be a different one of electrodes 114A, 114B, 116, 118, 120A, 120B, 128A, 128B, 128C, 128D, or the can 106 itself.

The sensing circuit 202 can be coupled to a tachyarrhythmia detection circuit 204. The tachyarrhythmia detection circuit can be configured to detect tachyarrhythmia in a patient, such as by using heart rate or morphology information from the depolarizations sensed by the sensing circuit 202. When the tachyarrhythmia detection circuit 204 detects the presence of a tachyarrhythmia, a processor 206 can be used to establish an ACP in response to and during the tachyarrhythmia. To establish the ACP, first, the sensing circuit 202 can be used to sense an intrinsic electrical heart depolarization at the first electrode and to sense an intrinsic electrical heart depolarization at the second electrode. The intrinsic electrical heart depolarization sensed at the first electrode can be the same intrinsic electrical heart depolarization sensed at the second electrode, or the intrinsic electrical heart depolarization sensed at the first electrode can be a different depolarization than the depolarization sensed at the second electrode.

Both the sensing circuit 202 and the tachyarrhythmia detection circuit 204 can be coupled to the processor circuit 206. The processor circuit 206 can be configured to determine, in response to and during the tachyarrhythmia, an intrinsic first time delay between the sensing of the intrinsic electrical heart depolarization at the first electrode and the sensing of the intrinsic electrical heart depolarization at the second electrode. The processor circuit 206 can also be coupled to an electrostimulation generator circuit 208 and to an anti-tachyarrhythmia therapy circuit 210.

The electrostimulation generator circuit 208 can be configured to deliver a plurality of electrostimulations using the first electrode. The processor circuit 206 can be configured to trigger timing of the delivery, by the electrostimulation generator circuit 208, of an individual electrostimulation in the plurality of electrostimulations, on a beat-by-beat basis, from a respective sensed intrinsic electrical heart depolarization at the second electrode. The individual electrostimulation is delivered at the first electrode after a specified second timing delay from the respective sensed intrinsic electrical heart depolarization at the second electrode. The second timing delay can be determined by the processor circuit 206 and can be adjustable over successive beats. The second timing delay can be specified to be approximately equal to the first time delay between the sensing of the intrinsic electrical heart depolarization at the first electrode and the sensing of the intrinsic electrical heart depolarization at the second electrode.

The processor circuit 206 can be configured to determine a second timing delay that, in an example, is within fifty percent of the first time delay. The processor circuit 206 can be configured to first determine a central tendency, such as a mean or median or like value, of a plurality of measurements of the first time delay, and to then determine a second timing delay that is shorter than the central tendency of the first time delay. The processor circuit 206 can be configured to determine a second timing delay that is a fixed and determined value, or to determine a second timing delay that is adjustable over time. For example, if the processor circuit 206 is configured to determine a second timing delay that is adjustable over time, the processor circuit 206 can be configured to decrease the second timing delay in a specified manner or in response to detecting a sensed intrinsic heart depolarization at the first electrode during the delivery of electrostimulations at the first electrode. This can tend promote electrostimulation-evoked depolarizations at the first electrode, and can tend to decrease sensed intrinsic depolarizations at the first electrode, thereby helping establish an ACP during the tachyarrhythmia, rather than intrinsic propagation during the tachyarrhythmia. In an example, the processor circuit 206 can be configured to gradually increase the second timing delay in response to an absence of sensed intrinsic heart depolarizations at the first electrode during the delivery of electrostimulations at the second electrode. This can tend to maintain the second timing delay at or near the intrinsic timing delay between the first and second electrodes, and can still promote electrostimulation-evoked depolarizations at the first electrode when used in conjunction with decreasing the second timing delay in response to detected intrinsic depolarizations at the first electrode during the delivery of the plurality of the electrostimulations at the ACP.

Figure 3:
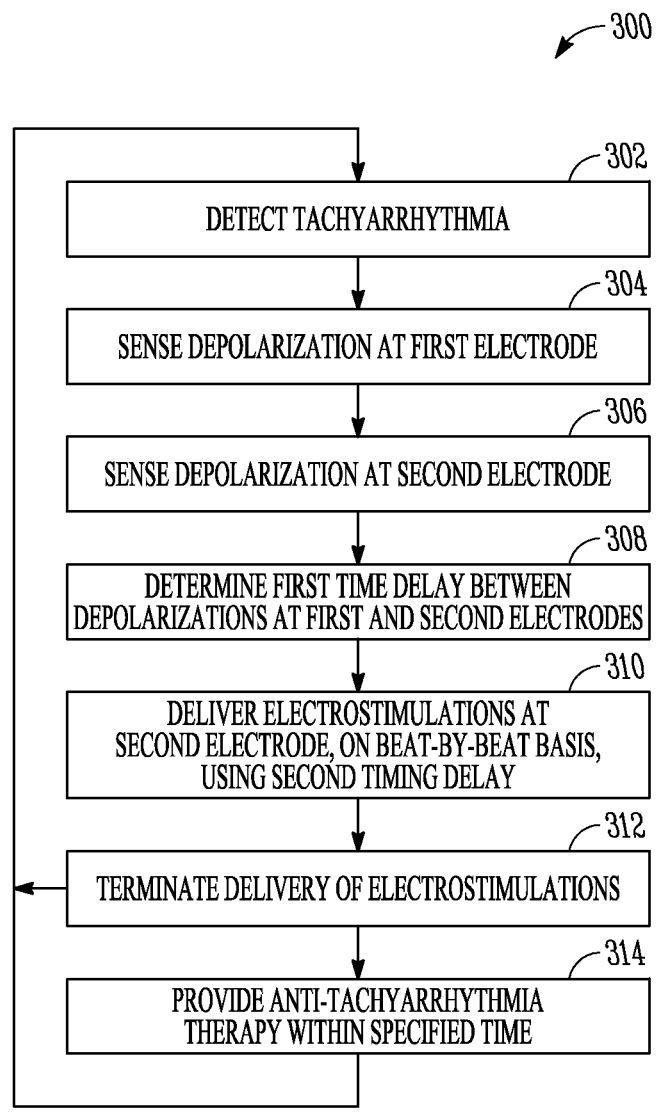
FIG. 3 illustrates an example of a method of using artificial conduction pathways in providing anti-tachyarrhythmia therapy.

FIG. 3 illustrates an example of a method 300 of using an ACP, such as for pre-conditioning the heart during a tachyarrhythmia in preparation for providing ATP, defibrillation, cardioversion, or other anti-tachyarrhythmia therapy. At 302, a tachyarrhythmia is detected. At 304, in response to and during the detected tachyarrhythmia, an intrinsic electrical heart depolarization is sensed at a first electrode at a first location at or in a heart of a patient. At 306, an intrinsic electrical heart depolarization is sensed at a second electrode a different second location at or in the heart. The intrinsic electrical heart depolarization sensed at the first electrode can be the same as the intrinsic electrical heart depolarization sensed at the second electrode, or the depolarization sensed at the first electrode can be a different depolarization than the one sensed at the second electrode. At 308, an intrinsic first time delay between the sensing of the depolarization at the first electrode and the depolarization at the second electrode is determined.

At 310, a plurality of electrostimulations is delivered, such as by using the first electrode. The delivery of electrostimulations can include triggering timing of the delivery of an individual electrostimulation in the plurality of electrostimulations, on a beat-by-beat basis, from a respective sensed intrinsic electrical depolarization at the second electrode. The timing of the delivery of an individual electrostimulation can include using a specified second timing delay from the respective sensed intrinsic electrical depolarization at the second electrode. The second timing delay can be specified to be approximately equal to the first time delay between the sensing of the depolarization at the first electrode and the depolarization at the second electrode. In an example, the second timing delay can be specified to be within fifty percent of the first time delay. A central tendency, such as a mean, median, or like value, of a plurality of measurements of the first time delay can be determined, and then the second timing delay can be specified to be shorter than the determined central tendency. The second timing delay is fixed and determined or adjustable over time. In an adjustable example, the second timing delay can be decreased in a specified manner or in response to a sensed intrinsic heart depolarization at the first electrode during the delivery of electrostimulations, such as described above. In addition, the second timing delay can be increased in response to an absence of sensed intrinsic heart depolarizations at the first electrode during the delivery of electrostimulations, such as described above.

The delivery of a plurality of electrostimulations at the first electrode, on a beat-by-beat basis, using the second timing delay, creates an ACP between the second electrode and the first electrode. The depolarization effectively propagated by this ACP can, in turn, be further propagated in various directions by cardiac cells near the first electrode. Multiple ACPs can be established and used concurrently, if desired. It is believed that an arrhythmia can incorporate the ACPs into the arrhythmic spatiotemporal depolarization propagation pattern. Eventually, it is believed that the tachyarrhythmia can become dependent or partially dependent on the ACPs, because it is believed that the ACPs, with their fixed or predictable timing cycles based on the specified second timing delay, can be conceptualized as more robust and reliable conduction pathways for the arrhythmia than the heart tissue itself without the ACPs. This can be conceptualized as pre-conditioning the tachyarrhythmia to prepare it for delivery of anti-tachyarrhythmia therapy—although it may be possible for the tachyarrhythmia to spontaneously terminate after the ACP is discontinued, in which case no anti-tachyarrhythmia therapy need be delivered.

At 312, delivery of electrostimulations using the ACPs can abruptly be discontinued. This removes one or more ACPs. Multiple ACPs can be withdrawn either simultaneously, or in an ordered sequence, such as according to the time at which each ACP was activated. It is believed that when one or more ACPs are suddenly removed, the tachyarrhythmia, which was previously rendered dependent on the ACPs, can either self-terminate or become more susceptible to anti-tachyarrhythmia therapy. Thus, after the termination of the ACP delivery of electrostimulations, there is expected to be a post-ACP interval of time when the tachyarrhythmia must somehow self-adjust to the sudden absence of one or more ACPs in order to sustain the tachyarrhythmia. During this post-ACP interval, it is believed that there is a transient increase in the amount of excitable tissue that would otherwise have been depolarized by the ACP, which, in turn, can allow anti-tachyarrhythmia therapy to be more effective, or can even result in termination of the tachyarrhythmia. Accordingly, at 314, anti-tachyarrhythmia therapy can provided within a specified time following termination of the delivery of electrostimulations—this can be conditioned upon determining whether the tachyarrhythmia persists after the ACP is removed. For example, the anti-tachyarrhythmia therapy can be provided within one cardiac cycle after and in response to discontinuing the delivery of electrostimulations. As another example, the anti-tachyarrhythmia therapy can be provided within two cardiac cycles (or other specified time period) after and in response to discontinuing the delivery of electrostimulations. The anti-tachyarrhythmia therapy can include at least one of anti-tachyarrhythmia pacing, defibrillation shock therapy, or cardioversion.

Figure 4:
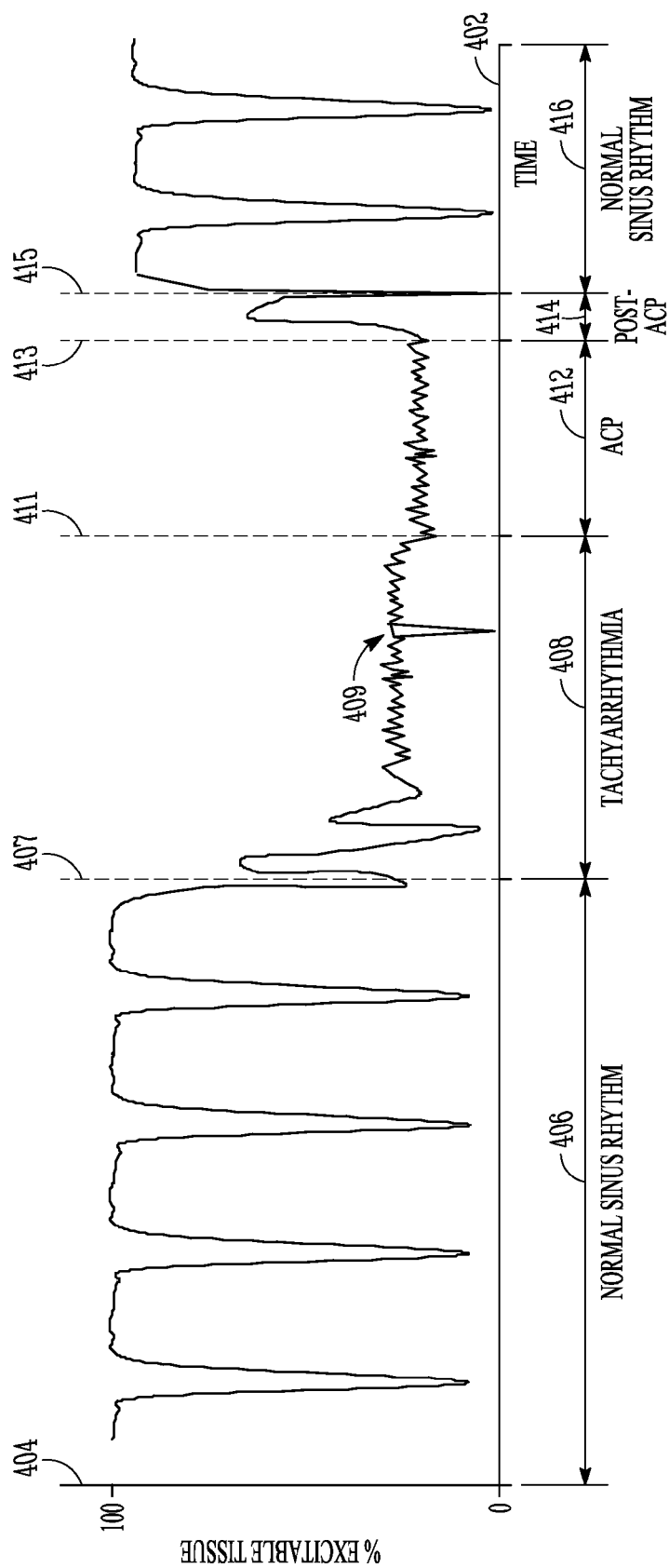
FIG. 4 is a graph illustrating an example of the hypothesized effects of an artificial conduction pathway on the electrical activity of a heart during tachyarrhythmia.

FIG. 4 is a graph illustrating an example of the hypothesized effects of an artificial conduction pathway on the electrical activity of a heart during tachyarrhythmia. In this example, the x-axis 402 represents time, and the y-axis 404 represent the percentage of cardiac tissue that is electrically excitable. Section 406 of the graph represents a period of normal sinus rhythm. During normal sinus rhythm, the percentage of cardiac tissue that is electrically excitable can vary fairly periodically between 0% and 100% in response to the depolarization and repolarization of a normal cardiac cycle. For example, when 100% of the cardiac tissue is electrically excitable, the heart is ready to be depolarized. Similarly, when 0% of the cardiac tissue is electrically excitable, the heart is completely depolarized.

At 407, the period of normal sinus rhythm 406 ends and a period of tachyarrhythmia 408 begins. During tachyarrhythmia, spatiotemporal propagation of cardiac tissue depolarizations generally continuously changes or varies, and the percentage of electrically excitable cardiac tissue at any given time is generally low. During the tachyarrhythmia period 408, shock therapy can be delivered at 409, such as by using the IMD 105. In this example, the shock therapy delivered at 409 is ineffective, as the period of tachyarrhythmia 408 continues immediately after the shock is delivered at 409.

At 411, one or more ACPs is initiated, marking the start of the ACP period 412. The one or more ACPs can be initiated according to method 300 described above with respect to FIG. 3. The ACP period 412 in this example is shown with a slightly lower degree of excitable tissue than the tachyarrhythmia period 408. The lower degree of excitable tissue is representative of the ACP's ability to excite tissue in advance of intrinsic arrhythmic activation, which is believed to be due to the ACP's fixed and predictable timing.

At 413, the one or more ACPs is suddenly discontinued, marking the start of the post-ACP period 414. During the post-ACP period 414, there can be a transient increase in the amount of excitable tissue that would otherwise have been depolarized by the ACP. It is believed that this transient increase in the amount of excitable cardiac tissue can provide a window of opportunity during the post-ACP period 414 in which anti-tachyarrhythmia therapy can be more effective. In other words, when the ACP is suddenly discontinued, such as at 413, the tachyarrhythmia must adjust to the absence of the ACP, upon which it may have become dependent or partially dependent. During the post-ACP period 414 of adjustment, a transient increase in the amount of excitable tissue (due to the sudden absence of the ACP) can result in an increase in the percentage of tissue that is susceptible to anti-tachyarrhythmia pacing, shock therapy, or defibrillation therapy, for example. Thus, the ACP period 412 can be conceptualized as pre-conditioning the tachyarrhythmia to prepare it for delivery of anti-tachyarrhythmia therapy during the post-ACP period 414—although it may be possible for the tachyarrhythmia to spontaneously terminate during the post-ACP period, in which case no anti-tachyarrhythmia therapy need be delivered.

At 415, shock therapy is delivered, such as by using IMD 105. In this example, the shock therapy delivered at 415 is effective, as a period of normal sinus rhythm 416 follows immediately after the delivery of the shock therapy at 415.

ADDITIONAL NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown and described. However, the present inventors also contemplate examples in which only those elements shown and described are provided.

All publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. §1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

What is claimed is:

1. An implantable medical device comprising:
a tachyarrhythmia detection circuit configured to detect a presence of a tachyarrhythmia in a subject;
a sensing circuit, coupled to the tachyarrhythmia detection circuit, and further coupled to a first electrode and a second electrode, wherein the first electrode is configured to be located at a first location in association with a heart of the subject and the second electrode is configured to be located at a second location in association with the heart, and wherein the sensing circuit is configured to sense, in response to and during the tachyarrhythmia, an intrinsic electrical heart depolarization at the first electrode and an intrinsic electrical heart depolarization at the second electrode;
a processor circuit, coupled to the sensing circuit and the tachyarrhythmia detection circuit, configured to:
determine an intrinsic first time delay between the sensing of the intrinsic electrical heart depolarization at the first electrode and the sensing of the intrinsic electrical heart depolarization at the second electrode;
determine a specified second timing delay, the specified second timing delay being at least one of fixed and determined, adjustable over time, within fifty percent of the determined intrinsic first time delay, or shorter than a central tendency of a plurality of measurements of the determined intrinsic first time delay; and an electrostimulation generator circuit, coupled to the processor circuit, configured to:

deliver a plurality of electrostimulations using the first electrode; and trigger delivery of each individual electrostimulation in the plurality of electrostimulations, on a beat-by-beat basis, according to the specified second timing delay timed from a respective sensed intrinsic electrical heart depolarization at the second electrode, wherein the delivery of the plurality of electrostimulations is configured to produce an artificial conduction pathway in the heart during tachyarrhythmia; and an anti-tachyarrhythmia therapy circuit, coupled to the processor circuit, configured to provide anti-tachyarrhythmia pacing within a specified number of cardiac cycles after and in response to termination of the delivery of the plurality of electrostimulations and discontinuation of the artificial conduction pathway.

2. The device of claim 1, wherein the intrinsic electrical heart depolarization sensed at the first electrode is the same intrinsic electrical heart depolarization sensed at the second electrode.

3. The device of claim 1, wherein the specified second timing delay from the respective sensed intrinsic electrical heart depolarization at the second electrode is specified to be within fifty percent of the determined intrinsic first time delay between the sensing of the intrinsic electrical heart depolarization at the first electrode and the sensing of the intrinsic electrical heart depolarization at the second electrode.

4. The device of claim 1, wherein the processor circuit is configured to determine the specified second timing delay, the specified second timing delay being a fixed and determined value.

5. The device of claim 1, wherein the processor circuit is configured to determine the specified second timing delay, the specified second timing delay being adjustable over time.

6. The device of claim 5, wherein the processor circuit is configured to decrease the specified second timing delay in response to a sensed intrinsic heart depolarization at the first electrode during the delivery of the plurality of electrostimulations, and wherein the processor circuit is configured to increase the specified second timing delay in response to an absence of a sensed intrinsic heart depolarization at the first electrode during the delivery of the plurality of electrostimulations.

7. The device of claim 1, wherein the processor circuit is configured to:

determine an intrinsic first time delay between the sensing of the intrinsic electrical heart depolarization at the first electrode and the sensing of the intrinsic electrical heart depolarization at the second electrode;

determine a central tendency of a plurality of measurements of the determined intrinsic first time delay; and determine the specified second timing delay, the specified second timing delay being shorter than a central tendency of the plurality of measurements of the determined intrinsic first time delay.

8. The device of claim 1, wherein the anti-tachyarrhythmia therapy circuit is configured to provide anti-tachyarrhythmia pacing within one cardiac cycle after and in response to the termination of the delivery of the plurality of electrostimulations.

9. The device of claim 1, wherein the anti-tachyarrhythmia therapy circuit is configured to provide anti-tachyarrhythmia pacing within two cardiac cycles after and in response to the termination of the delivery of the plurality of the electrostimulations.

10. An apparatus comprising:

means for determining that a tachyarrhythmia is present in a subject;

means for sensing, in response to and during the tachyarrhythmia, an intrinsic electrical heart depolarization at a first electrode that is located at a first location in association with a heart of the subject;

means for sensing, in response to and during the tachyarrhythmia, an intrinsic electrical heart depolarization at a second electrode that is located at a different second location in association with the heart;

means for determining an intrinsic first time delay between the sensing of the intrinsic electrical heart depolarization at the first electrode and the sensing of the intrinsic electrical heart depolarization at the second electrode;

means for determining a specified second timing delay, the specified second timing delay being at least one of fixed and determined, adjustable over time, within fifty percent of the determined intrinsic first time delay, or shorter than a central tendency of a plurality of measurements of the determined intrinsic first time delay;

means for delivering a plurality of electrostimulations using the first electrode, including triggering delivery of each individual electrostimulation in the plurality of electrostimulations, on a beat-by-beat basis, according to the specified second timing delay timed from a respective sensed intrinsic electrical heart depolarization at the second electrode, wherein the delivery of the plurality of electrostimulations is configured to produce an artificial conduction pathway in the heart during tachyarrhythmia; and means for providing anti-tachyarrhythmia pacing within a specified time after and in response to terminating the delivery of the plurality of electrostimulations and discontinuation of the artificial conduction pathway.

11. A method comprising:

determining that a tachyarrhythmia is present in a subject; and in response to and during the tachyarrhythmia:

sensing an intrinsic electrical heart depolarization at a first electrode that is located at a first location in association with a heart of the subject;

sensing an intrinsic electrical heart depolarization at a second electrode that is located at a different second location in association with the heart;

determining an intrinsic first time delay between the sensing of the intrinsic electrical heart depolarization at the first electrode and the sensing of the intrinsic electrical heart depolarization at the second electrode;

determining a specified second timing delay, the specified second timing delay being at least one of fixed and determined, adjustable over time, within fifty percent of the determined intrinsic first time delay, or shorter than a central tendency of a plurality of measurements of the determined intrinsic first time delay;

delivering a plurality of electrostimulations using the first electrode, including triggering delivery of each individual electrostimulation in the plurality of electrostimulations, on a beat-by-beat basis, according to the specified second timing delay timed from a respective sensed intrinsic electrical heart depolarization at the second electrode, wherein the delivery of the plurality of electrostimulations is configured to produce an artificial conduction pathway in the heart during tachyarrhythmia; and within a specified time after and in response to terminating the delivery of the plurality of electrostimulations and discontinuing of the artificial conduction pathway, providing anti-tachyarrhythmia pacing.

12. The method of claim 11, wherein sensing an intrinsic electrical heart depolarization at a first electrode and sensing an intrinsic electrical heart depolarization at the second electrode includes sensing the same intrinsic electrical heart depolarization at the first and second electrodes.

13. The method of claim 11, wherein the triggering the delivery of each electrostimulation in the plurality of electrostimulations includes the specified second timing delay being specified to be within fifty percent of the determined intrinsic first time delay between the sensing of the intrinsic electrical heart depolarization at the first electrode and the sensing of the intrinsic electrical heart depolarization at the second electrode.

14. The method of claim 11, wherein the triggering timing of the delivery of an individual electrostimulation in the plurality of electrostimulations includes the specified second timing delay being a fixed and determined value.

15. The method of claim 11, wherein the triggering timing of the delivery of an individual electrostimulation in the plurality of electrostimulations includes the specified second timing delay being adjustable over time.

16. The method of claim 15, comprising:

decreasing the specified second timing delay in response to a sensed intrinsic heart depolarization at the first electrode during the delivery of the plurality of electrostimulations; and increasing the specified second timing delay in response to an absence of a sensed intrinsic heart depolarization at the first electrode during the delivery of the plurality of electro stimulations.

17. The method of claim 11, comprising determining a central tendency of a plurality of measurements of the determined intrinsic first time delay, determining the specified second timing to be shorter than the central tendency of the plurality of measurements of the intrinsic first time delay.

18. The method of claim 11, wherein the providing anti-tachyarrhythmia pacing within a specified time after and in response to the termination of the delivery of the plurality of electrostimulations includes providing anti-tachyarrhythmia pacing within one cardiac cycle after the termination of the delivery of the plurality of electro stimulations.

19. The method of claim 11, wherein the providing anti-tachyarrhythmia pacing within a specified time after and in response to the termination of the delivery of the plurality of electrostimulations includes providing anti-tachyarrhythmia pacing within two cardiac cycles after the termination of the delivery of the plurality of the electrostimulations.

* * * * *